United States Patent [19]

Suh et al.

[11] Patent Number: 4,500,713

[45] Date of Patent: Feb. 19, 1985

[54] THERAPEUTIC DIPEPTIDES

[75] Inventors: John T. Suh, Greenwich, Conn.; Jeffrey N. Barton, New York; John R. Regan, Mamaroneck, both of N.Y.

[73] Assignee: USV Pharmaceutical Corporation, Tarrytown, N.Y.

[21] Appl. No.: 421,921

[22] Filed: Sep. 23, 1982

[51] Int. Cl.$^3$ .................. C07D 215/00; C07C 103/52
[52] U.S. Cl. .............................. 546/165; 260/112.5 R
[58] Field of Search ................. 260/112.5 R; 546/165

[56] References Cited

U.S. PATENT DOCUMENTS

| | | | |
|---|---|---|---|
| 3,842,064 | 10/1974 | Creven | 260/112.5 R |
| 3,850,904 | 11/1974 | Creven | 260/112.5 R |
| 4,104,371 | 8/1978 | Creven et al. | 260/112.5 R |
| 4,110,322 | 8/1978 | Creven et al. | 260/112.5 R |
| 4,344,949 | 8/1982 | Hoefle et al. | |
| 4,374,829 | 2/1983 | Harris et al. | 424/177 |
| 4,385,180 | 5/1983 | Kim et al. | 424/274 |

FOREIGN PATENT DOCUMENTS 2328453  5/1977  France ................ 260/112.5 R

OTHER PUBLICATIONS

Rec. des Tra. Chin. des Pays–Bas, vol. 98, pp. 168–172 (1979).

Primary Examiner—Delbert R. Phillips

[57] ABSTRACT

(3S)-2-N-[(1S)-1-Ethoxycarbonyl-1-(2,3-dihydro-1H-inden-2-yl)-methyl]-L-alanyl-1,2,3,4-tetrahydroisoquinoline-3-carboxylic acid is a antihypertensive agent.

1 Claim, No Drawings

THERAPEUTIC DIPEPTIDES

This invention relates to new compounds having valuable pharmacological activity. It particularly relates to compounds having antihypertensive and angiotensin converting enzyme inhibitory activity and the structure

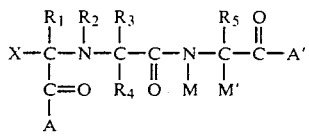

wherein

A and A' are independently hydroxy, lower alkoxy, lower alkenoxy, diloweralkylamino lower alkoxy, acrylamino lower alkoxy, acyloxy lower alkoxy, aryloxy, arloweralkyloxy, amino, loweralkylamino, diloweralkylamino, aryloweralkylamino, hydroxyamino, or substituted aryloxy, or substituted arloweralkoxy wherein the substituent is methyl, halo or methoxy;

$R_1$, $R_2$, $R_3$, $R_4$ and $R_5$ taken separately are each hydrogen, lower alkyl, lower alkenyl, lower alkynyl, aryl, fused aryl-cycloalkyl, aralkyl, cycloalkyl, heterocyclic, substituted alkyl, alkenyl, or alkynyl groups in which the substituents are hydroxy, alkoxy, halo, amino, aminoalkyl, alkylamino, mercapto, or alkylmercapto, substituted cycloalkyl groups in which the substituents are alkyl, halo, haloalkyl, hydroxy, alkylamino, nitro or trifluoromethyl, and substituted aryl and heterocyclic groups in which the substituents are alkyl, hydroxy, alkoxy, hydroxyalkyl, halo, mercapto, alkylmercapto, mercaptoalkyl, haloalkyl, amino, alkylamino, aminoalkyl, nitro, methylenedioxy, or trifluoromethyl;

$R_1$ and $R_2$ when taken together with the carbon and nitrogen to which they are respectively attached and $R_2$ and $R_3$ when taken together with the nitrogen and carbon to which they are respectively attached form an N-heterocyclic containing from 3 to 5 carbon atoms or 2 to 4 carbon atoms and a sulfur or nitrogen atom;

M is hydrogen, alkyl, alkenyl, alkynyl, cycloalkyl, cycloalkyl-alkyl, polycycloalkyl, polycycloalkyl-alkyl, aryl, aralkyl, heteroaryl, heteroaryl-alkyl, heterocycloalkyl, hetero-cycloalkyl-alkyl, fused aryl-cycloalkyl, fused aryl-cycloalkyl-alkyl, fused heteroaryl-cycloalkyl, fused heteroaryl-cycloalkyl-alkyl, alkoxyalkyl, alkylthioalkyl, alkylaminoalkyl, dialkylaminoalkyl;

M' is hydrogen, loweralkyl, cycloalkyl, phenyl, phenyl lower alkyl, hydroxy phenyl lower alkyl, hydroxy lower alkyl, amino lower alkyl, guanidino lower alkyl, imidazolyl lower alkyl, indolyl lower alkyl, mercapto lower alkyl or lower alkyl mercapto lower alkyl;

M and M' when taken together form an alkylene bridge of from 2 to 5 carbon atoms; an alkylene bridge of from 2 to 5 carbon atoms and one sulfur atom; an alkylene bridge of from 3 to 4 carbon atoms containing a double bond; a substituted alkylene bridge containing from 2 to 5 carbon atoms in which the substituent is hydroxy, lower alkoxy, or lower alkyl; or fused aralkylene;

M and M' when taken with the carbon and nitrogen to which they are respectively attached form a tetrahydroisoquinoline, dihydroindole or pyrrolidine ring;

X is

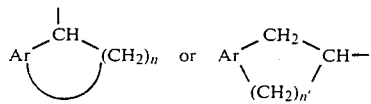

wherein
n = 2, 3 or 4;
n' = 1, 2 or 3; and

Ar is arylene or substituted arylene containing one or two substituents halo, $CF_3$, lower alkyl, OH, loweralkoxy, mercapto, amino or sulfamyl; and pharmaceutically-acceptable salts thereof.

The alkyl groups in alkyl per se, aralkyl, alkoxy, aminoalkyl, thioalkyl, haloalkyl, and hydroxyalkyl are preferably lower alkyl containing 1 to 6 carbon atoms and may be branched or straight chain.

The alkenyl and alkynyl groups contain from 2 to 6 carbon atoms and may be branched or straight chain.

The alkyl, alkenyl, and alkynyl groups may be substituted with substituents such as hydroxy, alkoxy, halo, amino, alkylamino, mercapto and alkylmercapto.

The cycloalkyl and cycloalkyl groups contain from 3 to 7 carbon atoms in the ring. Such cycloalkyl groups may be substituted with substituents such as alkyl, halo, haloalkyl, hydroxy, hydroxyalkyl, alkoxy, amino, aminoalkyl, alkylamino, trifluoromethyl, and nitro.

The aryl groups may have from 6 to 10 carbons and include phenyl and α- and β-naphthyl. The aryl groups may contain substituents such as alkyl, hydroxy, alkoxy, hydroxyalkyl, mercapto, alkylmercapto, mercaptoalkyl, halo, haloalkyl, amino, alkylamino, aminoalkyl, nitro, methylenedioxy, trifluoromethyl, ureido, and guanidino.

The fused aryl-cycloalkyl comprise phenyl rings fused to cycloalkyl rings having from 3 to 7 carbon atoms. These groups also include fused aryl-cycloalkyl-aryl.

The heterocyclic group per se, and in the heterocyclicalkyl may be saturated, partially saturated or unsaturated and includes such groups as pyridine, piperidine, morpholine, pyrrole, pyrrolidine, thiomorpholine, quinoline, isoquinoline, tetrahydroquinoline, thiazolidine, thiazoline, thiazole, imidazolidine, imidazoline, imidazole, thiophene, tetrahydrothiophene, furyl, tetrahydrofuran, and the like, These heterocyclic groups may also contain substituents as described for the aryl groups above. The heterocyclic group also includes heterocyclic lower alkyl.

The halo groups include fluorine, chlorine, bromine and iodine.

Suitable acid addition salts include inorganic salts such as hydrochloride, phosphate and sulfate; organic carboxylates such as acetate, malate, maleate, fumarate, succinate, citrate, lactate benzoate, hydroxybenzoate, aminobenzoate, nicotinate, and the like, and organic sulfonic and phosphonic acids such as toluenesulfonic acid.

Suitable basic salts include alkali and alkaline earth metal salts such as lithium, sodium, potassium, magnesium and calcium and iron, as well as ammonium and quarternary ammonium salts.

It is to be understood that the compounds of the present invention may have one or more asymmetric carbon atoms and the various racemic mixtures as well as the individual optically active compounds are considered to be within the scope of the present invention.

The compounds of the present invention may be prepared by amide forming reaction of an amine compound of the formula

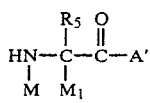  II with an acylating derivative of the acid of the formula:

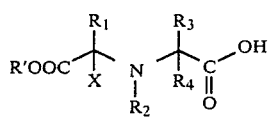  III in which $R^1$ is an alkyl, preferably lower alkyl, group.

Alternatively, the compounds in which $R_1$ and $R_2$ are hydrogen may be readily prepared by treating a compound of formula II with a compound of the formula

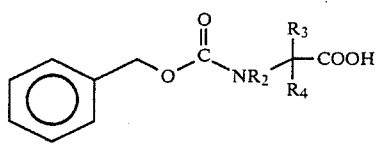  IV under amide-forming conditions to form a compound of the structure

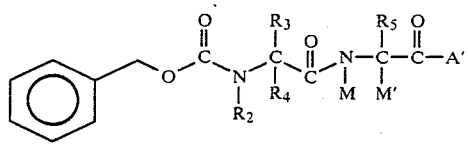  V splitting off the carbobenzyloxy group to give a free amine of the structure

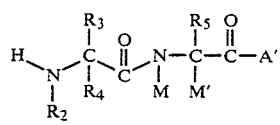  VI reacting the amine with an β-keto acid or ester of the formula

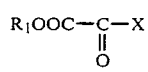  VII and reducing the resulting imine to give a compound of formula I wherein $R_3$ and $R_4$ are hydrogen.

Compounds of formula VI can also be reacted with an α-halo acid or ester of the formula

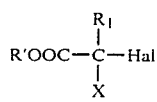  VIII to give compounds of formula I wherein $R_1$ and $R'$ can be H or any of the other substituents descriptive of the said $R_1$ and $R'$.

In the above sequence of reactions $R_1$ to $R_5$, M, M' and n are as hereinbefore defined and Hal is halogen.

Preferably, $R_1$, $R_2$, $R_3$, $R_4$ and $R_5$ are hydrogen and $R_2$ is lower alkyl or phenyl-lower alkyl, $R_6$ is lower alkyl.

The amide forming conditions referred to herein involve the use of known acylating derivatives of the described acids, such as the acyl halides, anhydrides, N-carboxyanhydrides, mixed anhydrides, lower alkyl esters, carbodiimides, carbonyl diimidazoles, and the like. The reactions are carried out in organic solvents such as acetonitrile, tetrahydrofuran, dioxane, acetic acid, methylene chloride, ethylene chloride and similar such solvents. The amide forming reaction will occur at room temperature or at elevated temperature. The use of elevated temperature is for convenience in that it permits somewhat shortened reaction periods. Temperatures ranging from 0° C. up to the reflux temperature of the reaction system can be used. As a further convenience the amide forming reaction can be effected in the presence of a base such as tertiary organic amines, e.g., trimethylamine, pyridine, picolines and the like, particularly where hydrogen halide is formed by the amide-forming reaction, e.g., acyl halide and amide compound. Of course, in those reactions where hydrogen halide is produced, any of the commonly used hydrogen halide acceptors can also be used.

In the condensation of an alpha haloacid derivative of formula VIII herein, similar reaction conditions, solvents and hydrogen halide acceptors can be used as for amide formation.

Various substituents on the present new compounds, e.g., as defined for $R_1$, can be present in the starting compounds or added after formation of the amide products by the known methods of substitution or conversion reactions. Thus, the nitro group can be added to the final product by nitration of the aromatic ring and the nitro group converted to other groups, such as amino by reduction, and halo by diazotization of the amino group and replacement of the diazo group. Other reactions can be effected on the formed amide product. Amino groups can be alkylated to form mono and dialkylamino groups, mercapto and hydroxy groups can be alkylated to form corresponding ethers. Thus, substitution or alteration reactions can be employed to provide a variety of substituents throughout the molecule of the final products. Of course, reactive groups where present should be protected by suitable blocking groups during any of the aforesaid reactions particularly the condensation reactions to form the amide linkages.

The acid and base salts of the present new compounds can be formed using standard procedures. Often, they are formed in situ during the preparation of the present new amido amino acids.

The present compounds obviously exist in stereoisomeric forms and the products obtained thus can be mixtures of the isomers, which can be resolved. Alternatively, by selection of specific isomers as starting compounds, the preferred stereoisomer can be produced. Therefore, the preferred forms, where each asymmetric center (chiral center) is S-configuration, are preferably prepared by the stereospecific route rather than attempting resolution of mixtures of isomers. The compounds in which the S-configuration exists at all asymmetric centers are the most active; in those in which the R-configuration exists are of less activity; and those where both R- and S-configurations exist are of intermediate activity.

The invention is further illustrated by the following examples.

EXAMPLE I

N-[1-Ethoxycarbonyl-1-(2,3-dihydro-1H-inden-2-yl)-methyl]alanyl-1,2,3,4-tetrahydro isoquinoline-3-carboxylic acid hydrochloride (A) 2-Bromoindane To 80 gms of 2-indanol in 200 ml of chloroform was added 12 ml of pyridine. The solution was cooled to 0° C. with an ice bath, and 64 ml of phosphorous tribromide slowly added over 30 minutes. The ice bath was removed, and the solution was refluxed for 1 hour, and let stand overnight.

The three phase system (two liquids and a solid) was poured onto 450 gms of ice. The layers were separated, the aqueous layer was extracted with 100 ml of chloroform, the combined organics were dried over magnesium sulfate, filtered and the volatiles removed on the rotavapor. The residue was distilled at reduced pressure. Yield 80 gms.

(B) 1,2,3,4-Tetrahydro-3-isoquinolinecarboxylic Acid

Phenylalanine (75 g) was refluxed with 488 ml of concentrated HCl and 165 ml of formalin for 30 minutes. Then a further 165 ml of HCl and 75 ml of formalin were added and the mixture refluxed for six more hours. After cooling, it was filtered, washed with a small amount of methanol, and dried overnight in a vacuum oven. This material was then treated for an hour with refluxing isopropanol and filtered after cooling to give 28 gms.

(C) S-1,2,3,4-Tetrahydro-3-isoquinolinecarboxylic Acid Benzyl Ester L-Tartrate

The amino acid hydrochloride (22.4 g) was refluxed with 22.4 g of p-toluenesulfonic acid and 20.8 gms of benzyl alcohol in 100 ml of toluene for two hours. After dilution with ether, the precipitate was removed by filtration. Addition of 10% NaOH led to the solution of most of this material, so after washing with ether, the aqueous layer was neutralized and filtered. This material was re-subjected to the esterification procedure. Now, most of the ensuing precipitate when partitioned between 10% NaOH and ether, went into the ether layer. This was combined with the original ether layer, washed with water and brine, dried over $MgSO_4$, filtered and stripped. The oily residue was triturated with 400 ml of acetonitrile, and six grams of L-tartaric acid added to the filtered solution. This suspension was heated on a steam bath to give a clear solution, from which 13.4 gms of product was obtained upon cooling.

(D) N-[1-Ethoxycarbonyl-1-(2,3-dihydro-1H-inden-2-yl)-methyl]alanyl-1,2,3,4-tetrahydro-3-isoquinolinecarboxylic Acid Benzyl Ester Benzyl L-1,2,3,4-tetrahydroisoquinoline-3-carboxylate-L-tartrate (1.5 g) was partitioned between 5% $NaHCO_3$ and $CH_2Cl_2$. The organic layer was separated, dried over $MgSO_4$, filtered, and added to 1 gram of N-[1-ethoxycarbonyl-1-(2,3-dihydro-1H-inden-2-yl)methyl]alanine (prepared as in Example 5) and 0.9 gm of HOBt. After solution occured, 0.8 gm of DCC was added with the almost immediate formation of a precipitate. After stirring for 2.5 hours, the precipitate was removed by suction filtration and the filtrate was washed with water, dried over $MgSO_4$, filtered and stripped.

This material was purified by column chromatography with $CH_2Cl_2$ followed by ether. Yield was about one gram.

EXAMPLE 2

N-[1-Ethoxycarbonyl-1-(2,3-dihydro-1H-inden-2-yl)-methyl]alanyl-1,2,3,4-tetrahydro-3-isoquinolinecarboxylic Acid Hydrochloride To a solution of D (1 gm) in 200 ml of ethanol was added 1 gm of 5% Pd/C. Then ammonium formate (0.6 gm) was added and the mixture stirred for 0.5 hours. The filtrate from a suction filtration was stripped under vacuum, and the residue taken up in ethyl acetate. This solution was washed with water and brine, then dried over $MgSO_4$, filtered and stripped. The residue was taken up in ether, filtered, and ethereal HCl added to the filtrate. The precipitate was filtered, washed with water, dissolved in $CH_2Cl_2$, filtered, dried over $MgSO_4$, filtered and stripped. The residue was twice treated as follows. After dissolution in ethyl acetate, it was washed with water, brine (several times), water and brine. The second time, the solution was treated with charcoal and filtered through celite. After removing the solvent from the filtrate of the $MgSO_4$ drying, the residue was taken up in ether, filtered, and ethereal HCl added. Removal of the solvent on a rotavapor gave a small amount of the product, mp 112°–118° C.

EXAMPLE 3

N-[1-Ethoxycarbonyl-1-(2,3-dihydro-1H-inden-2-yl)-methyl]alanyl-(N'-2,3-dihydro-1H-inden-5-yl)-glycine Using examples given above, N-[1-Ethoxycarbonyl-1-(2,3-dihydro-1H-inden-2-yl)-methyl]-alanine and N-2,3-dihydro-1H-inden-5-yl-glycine benzyl ester are reacted and the resulting N-[1-Ethoxycarbonyl-1-(2,3-dihydro-1H-inden-2-yl)-methyl]-alanyl-N'-(2,3-dihydro-1H-inden-5-yl)-glycine benzyl ester was treated with hydrogen in the presence of palladium on charcoal to give the title compound.

EXAMPLE 4

N-[1-Ethoxycarbonyl-1-(2,3-dihydro-1H-inden-2-yl)-methyl]alanyl-3-thioproline

Using examples given above, N-[1-Ethoxycarbonyl-1-(2,3-dihydro-1H-inden-2-yl)-methyl]-alanine and 3-thioproline benzyl ester are reacted and the resulting N-[1-Ethoxycarbonyl-1-(2,3-dihydro-1H-inden-2-yl)-methyl]-alanyl-3-thioproline benzyl ester was treated with hydrogen in the presence of palladium on carbon to give the title compound.

EXAMPLE 5

Synthesis of
N-[1-Ethoxycarbonyl-1-(2,3-dihydro-1H-inden-2-yl)-methyl]alanylproline hydrochloride A. Ethyl 2-cyano-2-acetamido-2-(2,3-dihydro-1H-inden-2yl)acetate Sodium ethoxide (40 gms) was stirred in 1 L of dimethyl sulfoxide until solution was complete. Then, 100 g of ethyl acetamido-cyanoacetate was added, and again stirred until solution was complete. 2-Bromoindane (101 g) was slowly added, using a few ml of DMSO to wash the container and addition funnel. The solution was stirred over a weekend.

The DMSO was distilled off under reduced pressure, and the oily residue partitioned between water and methylene chloride. The aqueous layer was washed with $CH_2Cl_2$, the combined organics poured over $MgSO_4$, charcoal was added, and the whole filtered. Removal of the $CH_2Cl_2$ on the rotavapor left a slightly colored solid which was recrystallized from methanol/water to give 81 gms. mp 160–162.

B. 2-Amino-2,3-Dihydro-1H-inden-2-ylacetic Acid

The product of paragraph A (81 g) was refluxed overnight in a mixture of 500 ml of $H_2O$ and 200 ml of concentrated hydrochloric acid. After cooling, it was filtered through Celite, made slightly basic with ammonium hydroxide, cooled for several hours in an ice bath, filtered, and dried overnight in a vacuum oven at 60° C. to give 69 gms of the amino acid. mp 300° C.

C. Ethyl 2-Amino-2,3-dihydro-1H-inden-2-ylacetate

The amino acid from paragraph B was suspended in 400 ml of ethanol saturated with hydrogen chloride gas. After the addition of a further 400 ml of ethanol, the mixture was refluxed over a weekend. After cooling, the solution was filtered, and the solvent removed. Addition of ether gave a precipitate which was filtered. Of several recrystallization attempts, the best was $CH_2Cl_2$/ether. Yield 40 g.

D. N-[1-Ethoxycarbonyl-1-(2,3-dihydro-1H-inden-2-yl)-methyl]alanine Benzyl Ester Benzyl 2-iodopropionate (obtained from 36.8 gms of the corresponding bromo compound by reaction with NaI/acetone) was dissolved in 350 ml of acetonitrile and 22 ml of triethylamine. The amino ester (from paragraph C) hydrochloride (21.5 g) was added and refluxed overnight. After stripping, it was taken up in ethyl acetate, and washed 3 times with $H_2O$, 5% $Na_2S_2O_3$, and brine. The organic layer was dried over $MgSO_4$, filtered and stripped. HPLC chromatography with $CH_2Cl_2$ gave 15 gms. Washing the column with EtOAc allowed the recovery of starting amino ester.

E. N-[1-Ethoxycarbonyl-1-(2,3-dihydro-1H-inden-2-yl)methyl]alanine

To 15 gms of the product of paragraph D in 250 ml of ethanol was added 1.5 g of 5% Pd/C. This mixture was hydrogenated overnight to obtain the product.

F. N-[1-Ethoxycarbonyl-1-(2,3-dihydro-1H-inden-2-yl)-methyl]alanylproline benzyl ester Proline benzyl ester hydrochloride (0.8 g) was dissolved in 5% sodium bicarbonate solution, and extracted with $CH_2Cl_2$. This solution was dried over $MgSO_4$, and filtered. To this was added 1 gm of paragraph E product, and 0.9 gm of 1-hydroxybenzotriazole. After a minute or so, the solution cleared, and 0.8 g of dicyclohexylcarbodiimide was added. The mixture was stirred for 3 hours, then a few drops of acetic acid and water were added and stirred a few minutes. After filtering, the solution was washed with $H_2O$, dried over $MgSO_4$, filtered and stripped. wt. 1.1 gm.

G. N-[1-Ethoxycarbonyl-1-(2,3-dihydro-1H-inden-2-yl)-methyl]alanylproline Hydrochloride To 1.1 gm of the paragraph F product in 200 ml of EtOH was added 1 gm of 5% Pd/C. This was hydrogenated in a Parr apparatus for 0.5 hours, then filtered and stripped. The oily residue was dissolved in 5% HCl, and extracted with ether. The aqueous layer was lyophilized. The solid residue was partitioned between $CH_2Cl_2$ and brine, and the aqueous layer exhaustively extracted with $CH_2Cl_2$. The combined organics were dried over $MgSO_4$, filtered and dried to give 0.1 gm of product.

EXAMPLE 6

N-[1-Ethoxycarbonyl-1-(2,3-dihydro-1H-inden-2-yl)methyl]-(4-pyridyl)alanylglycine Using examples given above, N-[1-Ethoxycarbonyl-1-(2,3-dihydro-1H-inden-2-yl)-methyl]-(4-pyridyl)-alanine and glycine benzyl ester are reacted and the resulting N-[1-Ethoxycarbonyl-1-(2,3-dihydro-1H-inden-2-yl)-methyl]-(4-pyridyl)-alanyl-glycine benzyl ester treated with hydrogen in the presence of palladium on carbon to give the title compound.

The following compounds are prepared employing the procedures of the preceding examples:

N-[1-Ethyoxycarbonyl-1-(2,3-dihydro-1H-inden-2-yl)-methyl]-alanyl-proline

2-N-[1-Ethoxycarbonyl-1-(2,3-dihydro-1H-inden-2-yl)-methyl]-alanyl-1,2,3,4-tetrahydroisoquinoline-3-carboxylic acid N-(2,3-Dihydro-1H-inden-5-yl)-N-[N-[1-ethoxycarbonyl-1-(2,3-dihydro-1H-inden-2-yl-methyl]-alanyl]glycine N-Cyclopentyl-N-[N-[1-ethoxycarbonyl-1-(2,3-dihydro-1H-inden-2-yl)-methyl]-alanyl]glycine 1-N-[1-Ethoxycarbonyl-1-(2,3-dihydro-1H-inden-2-yl)-methyl]-alanyl-2,3-dihydroindole-2-carboxylic acid N-[(1S)-1-Ethoxycarbonyl-1-(2,3-dihydro-1H-inden-2-yl)-methyl]-L-alanyl-L-proline (3S)-2-N-[(1S)-1-Ethoxycarbonyl-1-(2,3-dihydro-1H-inden-2-yl)methyl]-L-alanyl-1,2,3,4-tetrahydroisoquinoline-3-carboxylic acid N-(2,3-Dihydro-1H-inden-5-yl)-N-[N-(1S)-1-ethoxycarbonyl-1-(2,3-dihydro-1H-inden-2-yl)-methyl]-L-alanyl]glycine N-Cyclopentyl-N-[N-[(1S)-1-ethoxycarbonyl-1-(2,3-dihydro-1H-inden-2-yl)-methyl]-L-alanyl]glycine (2S)-1-N-[(1S)-1-Ethoxycarbonyl-1-(2,3-dihydro-1H-inden-2-yl)-methyl]-L-alanyl-2,3-dihydroindole-2-carboxylic acid.

The present new compounds demonstrate higher angiotensin converting enzyme inhibition, (ACEI activity) which is of a duration substantially longer with a fused arylcycloalkyl in place of an aralkyl group as substituent X. Exemplary of this higher activity and longer duration is a comparison of a phenethyl ACE inhibitor with the corresponding 2-indanyl compound in standard tests employed for determination of ACEI activity:

| Dose | Inhibition (%) | Duration (hrs.) |
|---|---|---|
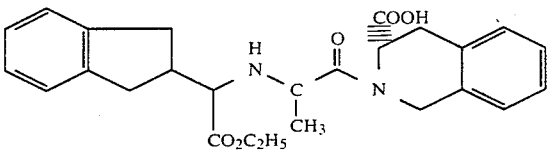
| 30 mg/kg (P.O.) | 91–78 | 4–5 |
| 10 mg/kg (P.O.) | 78–84 | 1–3 |

| Dose | Inhibition (%) | Duration (hrs.) |
|---|---|---|
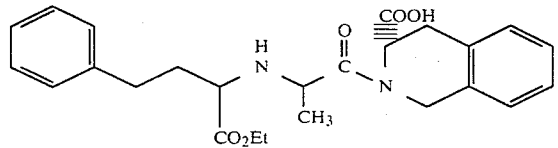
| 70 mg/kg (I.P.) | 45 | 1 |
| 10 mg/kg (P.O.) | 33–64 | 0.67 |

The compounds may be administered orally or parenterally on the treatment of hypertension and it is within the professional judgement and skill of the practitioner to determine the amount to be administered. Suitable dosage forms include tablets, capsules, elixiers and injectables.

We claim:

1. (3S)-2-N-[(1S)-1-Ethoxycarbonyl-1-(2,3-dihydro-1H-inden-2-yl)-methyl]-L-alanyl-1,2,3,4-tetrahydroisoquinoline-3-carboxylic acid.

* * * * *